US008071530B2

(12) United States Patent
Smith

(10) Patent No.: US 8,071,530 B2
(45) Date of Patent: Dec. 6, 2011

(54) ORGANOLEPTIC COMPOUNDS AND THEIR USE IN PERFUME COMPOSITIONS

(75) Inventor: Catherine Marie Smith, Bayville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 563 days.

(21) Appl. No.: 11/464,403

(22) Filed: Aug. 14, 2006

(65) Prior Publication Data

US 2008/0039361 A1 Feb. 14, 2008

(51) Int. Cl.

| | |
|---|---|
| ***A61K 8/18*** | (2006.01) |
| ***C07C 41/00*** | (2006.01) |
| ***A61Q 13/00*** | (2006.01) |

(52) U.S. Cl. ................. 512/20; 512/25; 512/1; 568/579

(58) Field of Classification Search .................... 512/20, 512/25, 1; 568/579

See application file for complete search history.

(56) References Cited

U.S. PATENT DOCUMENTS 4,604,487 A * 8/1986 Wiegers et al. ............... 568/715

OTHER PUBLICATIONS

Cram et al. "Studies in Stereochemistry. XXXVI Radical Anions as Neighboring and Electron Transfer Groups in Substitution-Reduction Reactions" CAOLD, Nov. 2, 1962 vol. 85; Chemical Abstracts pp. 1268-1273.*

Cram et al. "Studies in Stereochemistry. XXXVI Radical Anions as Neighboring and Electron Transfer Groups in Substitution-Reduction Reactions" CAOLD, Nov. 1962 vol. 85; Chemical Abstracts pp. 1268-1273.*

"The Substituent Effects on Solvolyses of threo-2-Aryl-lmethylopropyl Brosylates", Fujio et al, Bull. Chemical. Soc. Jpn., 65, 3072-3079 (1992), Vo;. 65, No. 11, Abstract.

Computer Structure Search, Benzene, (2-methoxy-l-methylbuty1)- and analogs (continued), Dec. 12, 2005, STN International Database.

"Gas-Phase Acid-Induced Nucleophilic Displacement Reactions. 7.[1] Structural and Stereochemical Evidence for the Existence and the Relative Stability of Alkylenebenzenium Ions in the Gas Phase", Fornarini et al., J. Am. Chem. Soc. 1988, 110, 34-41.

"Studies in Stereochemistry. XXXVI. Radical Anions as Neighboring and Electron Transfer Groups in Substitution-Reduction Reactions ", Cram et al., Contribution from Department of Chemistry of the University of California at Los Angeles. Los Angeles 24, Calif., Nov. 2, 2962, vol. 85.

194. Photochemische Umsetzung von optisch aktiven 2-(1'-Methylallyl)anilinen mit Methanol[1] ), Scholl et al., Helvetica Chimica Acta-vol. 63, Fasc.7 (1980)-Nr. 194, (12.VIII.80), pp. 1823-1833.

"Rapid Stereospecific Methylation of Alcohols and Glycols with Sodium Hydride/Methyl Iodide", Brown et al, Baker Chemistry Laboratory, Cornell University, Ithaca, New York 14850 U.S.A., S. Sivaram, Wetherill Chemistry Laboratory, Purdue University, Lafayette, Indiana 47907, U.S.A, Jan. 28, 1974, pp. 434-436.

* cited by examiner

*Primary Examiner* — Patrick Ryan
*Assistant Examiner* — Aaron Greso
(74) *Attorney, Agent, or Firm* — Elizabeth M. Quirk; XuFan Tseng; Joseph F. Leightner

(57) ABSTRACT

The present invention a method of improving, enhancing or modifying a fragrance formulation through the addition of an olfactory acceptable amount of the following compound:

Formula I

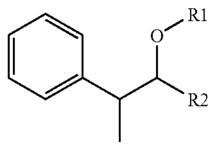

wherein $R^1$ and $R^2$ independently represent a straight, branched or cyclic hydrocarbon moiety consisting of less than 10, preferably less than 4, most preferably less than 2 carbon atoms.

3 Claims, No Drawings

ORGANOLEPTIC COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the fragrance compounds and a method of improving, enhancing or modifying a fragrance formulation through the addition of an olfactory acceptable amount of the Formula I set forth below:

Formula I

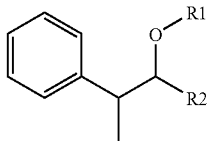

wherein $R^1$ and $R^2$ independently represent a straight, branched or cyclic hydrocarbon moiety consisting of less than 10, preferably less than 4, most preferably less than 2 carbon atoms.

Another embodiment of the invention is directed to a method for enhancing a perfume composition by incorporating an olfactory acceptable amount of the compounds provided above.

These and other embodiments of the present invention will be apparent by reading the following specification.

DETAILED DESCRIPTION OF THE INVENTION

In Formulae I above, $R^1$ and $R^2$ independently represent a hydrogen or a straight, branched or cyclic hydrocarbon moiety consisting of less than 15, preferably less than 10, most preferably less than 4 carbon atoms. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like.

Suitable hydrocarbon moieties containing double bonds include ethene, propene, 1-butene, 2-butene, penta-1-3-deine, hepta-1,3,5-triene and the like.

In another embodiment of the invention, the novel compounds of the invention are represented by the following structures:

Structure I

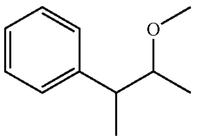

Structure II

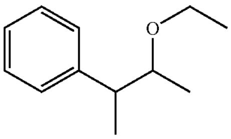

Structure III

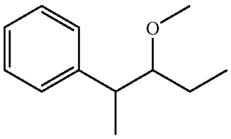

Structure IV

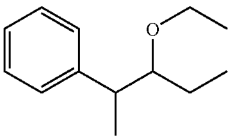

Those with the skill in the art will appreciate that the compound of Structure I is (2-methoxy-1-methylpropyl)-benzene; Structure II is (2-ethoxy-1-methylpropyl)-benzene; Structure III is (2-methoxy-1-methylbutyl)-benzene; and Structure IV is (2-ethoxy-1-methylbutyl)-benzene.

The compounds of the present invention may be prepared from the corresponding compounds via an ether formation of the following sequence:

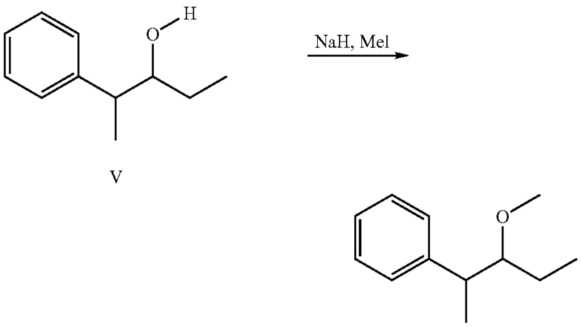

V

III

The starting materials for the above reaction are commercially available from Aldrich Chemical Company. Those with skill in the art will appreciate the following reagents abbreviated as NaH is sodium hydride, DMF is dimethyl formamide and MeI is iodomethane.

The starting material, alcohol V, was prepared according to the procedure described in Shumway, W.; Ham, S.; Moer, J.; Whittlesey, B.; Birney, D. *J. Org. Chem.* 2000, 65, 7731.

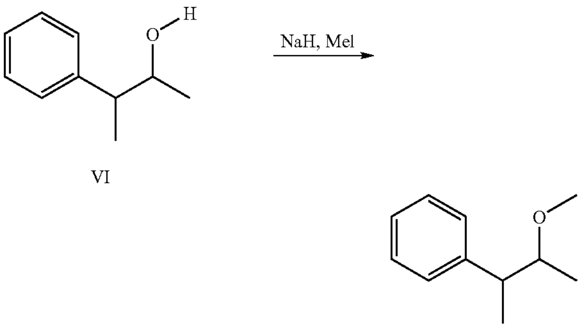

VI

I

The starting material, Alcohol VI, was prepared according to the procedure described in Alverez-Ibarra, C.; Arjona, O.; Perez-Ossorio, R.; Perez-Rubalcaba, A.; Quiroga, M.; Santesmases, M. *J. Chem. Perkin Trans.* 2 1983, 11, 1645.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

We have discovered that Structure I possesses floral, green, fruity, woody, wasabe fragrance notes. Structure III possesses green, floral, grapefruit, citrus, fruity, fresh, khusinil and spicy fragrance notes.

When used in a fragrance formulation this ingredient provides freshness making the fragrance top notes more desirable and noticeable. It also has a spicy peppery odor which is very commonly used in men's fragrances added for fragrance appropriateness and desirability. The woody part of it is very useful in both men's and women's fragrances adding body and substantivity to the finished product. All of these odor qualities found in this material assist in beautifying and enhancing the finished accord improving the performance of the other materials in the fragrance. The floral of it will beautify as well and makes the fragrance more desirable and add the perception of value. There is also the fruity side of it which is found in many fragrances today which happens to be very trendy, especially for the younger consumer.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams, NaH stands for sodium hydride, DMF stands for dimethylformamide, $NH_4Cl$ stands for ammonium chloride. IFF as used in the examples is understood to mean International Flavors & Fragrances Inc., New York, N.Y., USA.

Example I

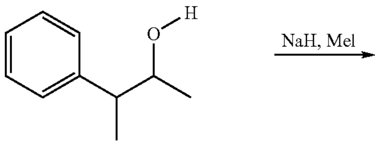

VI

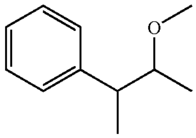

I (2-Methoxy-1-methyl-propyl)-benzene (Structure I): In a 2000 mL reaction flask is charged a 60% by weight in oil dispersion of NaH (32.0 g, 0.79 mol) and 500 mL of DMF under $N_2$. The mixture is heated to 40° C. and alcohol 1 (100 g, 0.66 mol) is fed to the reaction over 1 hour. The reaction is aged for 1 hours at 40° C., then iodomethane (113 g, 0.79 mol) is fed into the reaction over 2 hours. The reaction is aged for 8 hours, then quenched with 300 mL of saturated $NH_4Cl$ solution. The layers are separated and the organic layer is washed with 300 mL saturated $NaHCO_3$ and 300 mL of brine. The crude product was purified by distillation to give 101 g of ether I, 61% yield.

(2) (2-Methoxy-1-methyl-butyl)-benzene: $^{1}H$ NMR (500 MHz, $CDCl_3$) δ 7.34-7.17 (m, 5H), 3.35 (s, 3H), 3.42-3.3.30 (m, 1H), 2.78-2.58 (m, 1H), 1.32 (d, J=7.00 Hz, 3H), 0.97 (d, 3H).

NaH, DMF, and iodomethane were purchased from Aldrich Chemical Company. The starting material, Alcohol VI, was prepared according to the procedure described in Alverez-Ibarra, C.; Arjona, O.; Perez-Ossorio, R.; Perez-Rubalcaba, A.; Quiroga, M.; Santesmases, M. *J. Chem. Perkin Trans.* 2 1983, 11, 1645.

The compound was described as having floral, green, fruity and wasabe fragrance notes.

Example II

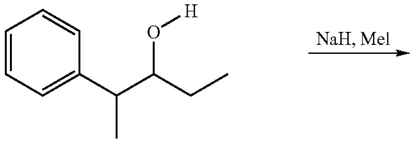

V

-continued

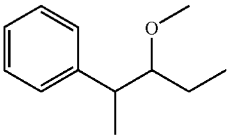

III (2-Methoxy-1-methyl-butyl)-benzene (Structure III): In a 2000 mL reaction flask is charged a 60% by weight in oil dispersion of NaH (29.5 g, 0.73 mol) and 500 mL of DMF under $N_2$. The mixture is heated to 40° C. and alcohol V (100 g, 0.61 mol) is fed to the reaction over 1 hour. The reaction is aged for 1 hours at 40° C., then iodomethane (103 g, 0.73 mol) is fed into the reaction over 2 hours. The reaction is aged for 8 hours, then quenched with 300 mL of saturated $NH_4Cl$ solution. The layers are separated and the organic layer is washed with 300 mL saturated $NaHCO_3$ and 300 mL of brine. The crude product was purified by distillation to give 63 g of ether III, 58% yield.

(2) (2-Methoxy-1-methyl-butyl)-benzene: $^{1}H$ NMR (500 MHz, $CDCl_3$) δ 7.34-7.17 (m, 5H), 3.34 (s, 2.25H), 3.28 (s, 0.75H), 3.20-3.13 (m, 1H), 2.97 (p, J=6.77 Hz, 0.25H), 2.84 (p, J=6.99 Hz, 0.75H), 1.49-1.40 (m, 1.5H), 1.30 (d, J=7.00 Hz, 2.25H), 1.25 (d, J=7.14 Hz, 0.75H), 1.35-1.23 (m, 0.5H), 0.89 (t, J=7.47 Hz, 0.75H), 1.85 (t, J=7.40 Hz, 2.25H). NaH, DMF, and iodomethane were purchased from Aldrich Chemical Company. The starting material, alcohol V, was prepared according to the procedure described in Shumway, W.; Ham, S.; Moer, J.; Whittlesey, B.; Birney, D. *J. Org. Chem.* 2000, 65, 7731. The compound was described as having green, floral, grapefruit, citrus, fruity, fresh, khusinil and spicy fragrance notes.

Example III

Demonstration Fragrance Formula with (2-methoxy-1-methyl-butyl)-benzene

| | |
|---|---|
| Aldehyde AA Triplal BHT | 5.00 |
| Allyl Amyl Glycolate | 10.00 |
| Amyl Sal | 15.00 |
| Benz Acet | 60.00 |
| Citronellol Couer | 15.00 |
| Citronellol Acet | 40.00 |
| Cyclamal Extra | 20.00 |
| Ethyl Linalool | 70.00 |
| Ionone Alpha | 10.00 |
| Ionone Beta Extra | 40.00 |
| Iso Gamma Super BHT | 50.00 |
| Kharismal | 20.00 |
| Lilial | 100.00 |
| Linalool Syn | 80.00 |
| Meth Ionone Gamma Coeur | 25.00 |
| Nebulone (Elinics) | 20.00 |
| Neryl Acet A | 40.00 |
| Orange Oil Fla Decol K-10930-01 “PFG” BHT | 75.00 |
| Phen Eth Alc White Extra | 100.00 |
| Sanjinol BHT | 5.00 |
| Terpineol Coeur | 55.00 |
| Undecalactone Gamma | 30.00 |
| Verdox | 55.00 |
| (2-methoxy-1-methylbutyl)-benzene | 60.00 |
| Total weight | 1000.00 |

What is claimed is:

1. A compound (2-ethoxy-1-methylbutyl)-benzene.

2. A fragrance formulation containing an olfactory effective amount of the compound of claim 1.

3. A fragrance product containing the compound of claim 1.

* * * * *